United States Patent [19]
Nakajima

[11] Patent Number: 5,229,618
[45] Date of Patent: Jul. 20, 1993

[54] RADIATION IMAGE READ-OUT APPARATUS COMPENSATING FOR IMAGE DISTORTION

[75] Inventor: Nobuyoshi Nakajima, Kanagawa, Japan

[73] Assignee: Fuji Photo Film Co., Ltd., Kanagawa, Japan

[21] Appl. No.: 778,659

[22] Filed: Oct. 18, 1991

[30] Foreign Application Priority Data

Oct. 20, 1990 [JP] Japan ................... 2-282339

[51] Int. Cl.$^5$ ..................... G01N 21/86; G01N 21/01
[52] U.S. Cl. ........................................ 250/559; 382/6; 356/444; 250/208.1
[58] Field of Search ............ 250/235, 236, 234, 208.1, 250/559, 571–572, 562–563, 327.02 G; 382/6, 54; 378/62, 98–99; 356/444, 443

[56] References Cited

U.S. PATENT DOCUMENTS

| | | | |
|---|---|---|---|
| 4,258,264 | 3/1981 | Kotera et al. | 250/484 |
| 4,276,473 | 6/1981 | Kato et al. | 250/327.1 |
| 4,302,672 | 11/1981 | Kato et al. | 382/6 |
| 4,315,318 | 2/1982 | Kato et al. | 364/515 |
| 4,317,179 | 2/1982 | Kato et al. | 382/6 |
| 4,387,428 | 6/1983 | Ishida et al. | 364/414 |
| 4,963,739 | 10/1990 | Hishinuma | 250/327.2 G |
| 4,994,662 | 2/1991 | Funahashi et al. | 250/208.1 |
| 4,999,497 | 3/1991 | Funahashi et al. | 250/327.2 G |
| 5,046,147 | 9/1991 | Funahashi et al. | 250/327.2 G |
| 5,068,907 | 11/1991 | Takeo | 382/6 |

FOREIGN PATENT DOCUMENTS 56-11395 2/1981 Japan.
61-5193 2/1986 Japan.

OTHER PUBLICATIONS

Chow, "Nonlinear Processor of Radiographic Images," IBM Tech., Disc. Bull. vol. 13, No. 11, Apr. 1971, pp. 3272–3273.

Primary Examiner—David C. Nelms
Assistant Examiner—Michael Messinger
Attorney, Agent, or Firm—Sughrue, Mion, Zinn Macpeak & Seas

[57] ABSTRACT

A radiation image read-out apparatus comprises a read-out section for photoelectrically reading out a radiation image from silver halide film, on which the radiation image has been recorded, and thereby generating an image signal representing the radiation image. A signal conversion device converts the image signal such that distortion in the image signal, which distortion is caused to occur by nonlinear characteristics of the silver halide film, may be eliminated. A corrected image signal is thereby obtained, which can be processed commonly with an image signal obtained by reading out a radiation image from a stimulable phosphor sheet, on which the radiation image has been stored.

4 Claims, 2 Drawing Sheets

RADIATION IMAGE READ-OUT APPARATUS COMPENSATING FOR IMAGE DISTORTION

BACKGROUND OF THE INVENTION

1. Field of the Invention

This invention relates to a radiation image read-out apparatus provided with a film digitizer for photoelectrically reading out a radiation image, which has been recorded on a sheet of silver halide film, and thereby generating an image signal representing the radiation image.

2. Description of the Prior Art

Techniques for reading out a recorded image in order to obtain an image signal, carrying out appropriate image processing on the image signal, and then reproducing a visible image by use of the processed image signal have heretofore been known in various fields.

For example, as disclosed in Japanese Patent Publication No. 61(1986)-5193, a sheet of X-ray film having a small gamma value chosen according to the type of image processing to be carried out is used together with an intensifying screen, and an X-ray image is recorded on the X-ray film. The X-ray film, on which the X-ray image has been recorded, is subjected to a developing process. The X-ray image is then read out from the X-ray film and converted into an electric signal (image signal). The image signal is processed and then used for reproducing the X-ray image as a visible image on a copy photograph or the like. In this manner, a visible image having good image quality with high contrast, high sharpness, high graininess, or the like, can be reproduced. The device for detecting the image signal from the film is usually referred to as a film digitizer (FD).

When certain kinds of phosphors are exposed to radiation such as X-rays, α-rays, β-rays, γ-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor.

As disclosed in U.S. Pat. Nos. 4,258,264, 4,276,473, 4,315,318, 4,387,428, and Japanese Unexamined Patent Publication No. 56(1981)-11395, it has been proposed to use stimulable phosphors in radiation image recording and reproducing systems. Specifically, a sheet provided with a layer of the stimulable phosphor (hereinafter referred to as a stimulable phosphor sheet) is first exposed to radiation which has passed through an object, such as the human body. A radiation image of the object is thereby stored on the stimulable phosphor sheet. The stimulable phosphor sheet is then scanned with stimulating rays, such as a laser beam, which cause it to emit light in proportion to the amount of energy stored thereon during its exposure to the radiation. The light emitted by the stimulable phosphor sheet, upon stimulation thereof, is photoelectrically detected and converted into an electric image signal. The image signal is then used during the reproduction of the radiation image of the object as a visible image on a recording material such as photographic film, on a display device such as a cathode ray tube (CRT) display device, or the like. Such radiation image recording and reproducing systems are usually referred to as computed radiography (CR).

CR systems which use stimulable phosphor sheets are advantageous over conventional radiography using silver halide photographic materials, in that images can be recorded even when the energy intensity of the radiation to which the stimulable phosphor sheet is exposed varies over a wide range. More specifically, since the amount of light which the stimulable phosphor sheet emits when being stimulated varies over a wide range and is proportional to the amount of energy stored thereon during its exposure to the radiation, it is possible to obtain an image having a desirable density regardless of the energy intensity of the radiation to which the stimulable phosphor sheet was exposed. In order to obtain the desired image density, an appropriate read-out gain is set when the emitted light is being detected and converted into an electric signal to be used in the reproduction of a visible image on a recording material, such as photographic film, or on a display device, such as a CRT display device.

The film digitizer systems (FD systems), which use X-ray film, and the computed radiography systems (CR systems), which use stimulable phosphor sheets, have been developed independently of each other. Therefore, in the past, no problem occurred from incompatibility between the FD systems and the CR systems.

However, recently, in a single large hospital, it often occurs that an FD system, which uses X-ray film, is introduced into a certain medical office, and a CR system, which uses stimulable phosphor sheets, is introduced into a different medical office. Also, it often occurs that an FD system, which uses X-ray film, is introduced into a certain hospital, and a CR system, which uses stimulable phosphor sheets, is introduced into a different hospital. In such cases, problems occur in that information interchange cannot be carried out smoothly between the medical office, into which the FD system has been introduced, and the medical office, into which the CR system has been introduced. Such problems also occur between the hospital, into which the FD system has been introduced and the hospital, into which the CR system has been introduced.

SUMMARY OF THE INVENTION

The primary object of the present invention is to provide a radiation image read-out apparatus, wherein a radiation image is read out from silver halide film, such as X-ray film, on which the radiation image has been recorded, and an image signal representing the radiation image is obtained such that the image signal may be processed commonly with an image signal obtained by reading out a radiation image from a stimulable phosphor sheet, on which the radiation image has been stored.

Another object of the present invention is to provide a radiation image read-out apparatus, which enables information interchange to be carried out smoothly between a location of an FD system, which uses silver halide film, and a location of a CR system, which uses stimulable phosphor sheets.

The present invention provides a radiation image read-out apparatus comprising:

i) a read-out section for photoelectrically reading out a radiation image from silver halide film, on which said radiation image has been recorded, and thereby generating an image signal representing said radiation image, and ii) a signal conversion means for converting said image signal such that distortion in said image signal, which distortion is caused to occur by nonlinear characteristics of said silver halide film, may be eliminated, and thereby generating a corrected image signal.

Silver halide photographic materials, such as X-ray film, have nonlinear characteristics such that the image density of a radiation image recorded on a silver halide photographic material is not proportional to the amount of energy recorded on the silver halide photographic material (or the energy intensity of the radiation to which the silver halide photographic material was exposed), which amount of energy (or which energy intensity) is plotted on a logarithmic scale. Therefore, an image signal obtained by reading out the radiation image from the silver halide photographic material includes distortion, which is caused to occur by the nonlinear characteristics of the silver halide photographic material. On the other hand, as described above, stimulable phosphor sheets have linear characteristics such that the amount of light, which a stimulable phosphor sheet carrying a radiation image stored thereon emits when being stimulated, is very accurately proportional to the amount of energy stored on the stimulable phosphor sheet during its exposure to the radiation. Therefore, an image signal obtained by detecting the light emitted by the stimulable phosphor sheet does not include the aforesaid distortion. For this reason, heretofore, image signals, which are obtained from FD systems, and image signals, which are obtained from CR systems, could not be utilized commonly with each other.

With the radiation image read-out apparatus in accordance with the present invention, after the image signal is obtained by reading out the radiation image, which has been recorded on the silver halide film, distortion in the image signal, which distortion is caused to occur by nonlinear characteristics of the silver halide film, is eliminated from the image signal. The corrected image signal is thereby obtained. Therefore, the corrected image signal, which has been obtained from the radiation image read-out apparatus in accordance with the present invention, can be utilized commonly with an image signal obtained by reading out a radiation image from a stimulable phosphor sheet, on which the radiation image has been stored. For example, the same image processing can be carried out on both the image signal, which has been obtained from the radiation image read-out apparatus in accordance with the present invention, and the image signal obtained by reading out the radiation image from the stimulable phosphor sheet, on which the radiation image has been stored.

DESCRIPTION OF THE PREFERRED EMBODIMENTS

The present invention will hereinbelow be described in further detail with reference to the accompanying drawings.

Figure 1:
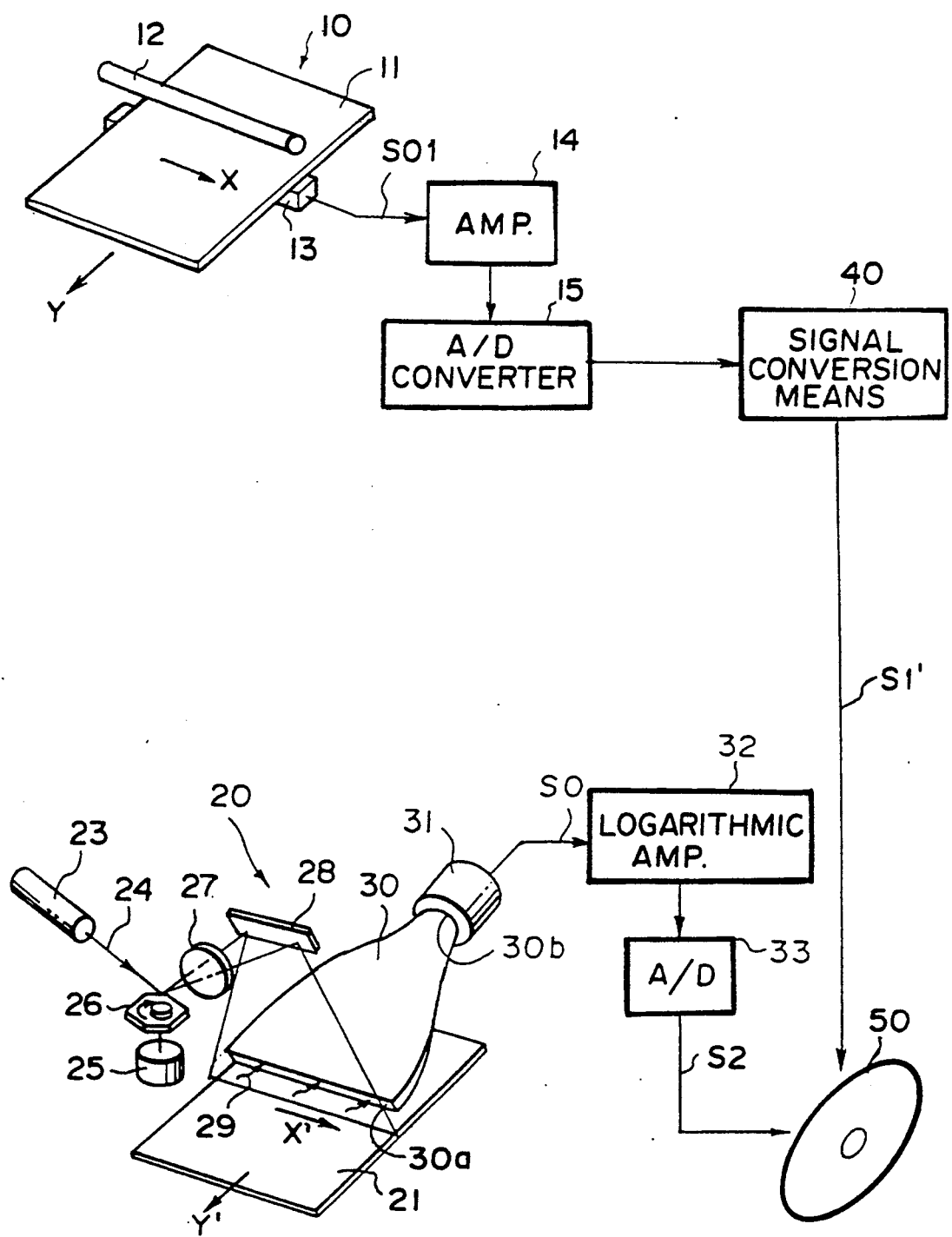
FIG. 1 is a perspective view showing an embodiment of the radiation image read-out apparatus in accordance with the present invention.

FIG. 1 is a perspective view showing an embodiment of the radiation image read-out apparatus in accordance with the present invention.

With reference to FIG. 1, in an X-ray image recording apparatus (not shown), an X-ray image has been recorded on an X-ray film 11. The X-ray film 11 has then been subjected to a developing process in a developing machine (not shown). The X-ray film 11 is set at a predetermined position in a first read-out section 10 and conveyed by a conveyance means (not shown) along a conveyance path in the direction indicated by the arrow Y. In the first read-out section 10, a lamp 12 is located above the conveyance path, along which the X-ray film 11 is conveyed. The lamp 12 linearly irradiates light to the X-ray film 11, which is located in the conveyance path. A line sensor 13, which may be constituted of a CCD array, or the like, is located on the side opposite to the lamp 12 with respect to the X-ray film 11 such that the line sensor 13 faces the lamp 12. When the X-ray film 11 is conveyed in the direction indicated by the arrow Y from a predetermined position and reaches the position between the lamp 12 and the line sensor 13, the light produced by the lamp 12 passes through the X-ray film 11. The intensity of the light, which has passed through the X-ray film 11, is modulated in accordance with the X-ray image recorded on the X-ray film 11. The light, which has passed through the X-ray film 11, is detected by the line sensor 13. In this manner, an analog image signal SO1 representing the image information recorded on a single line on the X-ray film 11, which line extends in the direction indicated by the arrow X, is obtained. By repeating the detection of the light while the X-ray film 11 is being conveyed in the direction indicated by the arrow Y, an analog image signal SO1 is obtained which represents the whole X-ray image recorded on the X-ray film 11. The image signal SO1 is then amplified by an amplifier 14 and converted by an A/D converter 15 into a first digital image signal S1. The first digital image signal S1 is fed into a signal conversion means 40.

Figure 2:
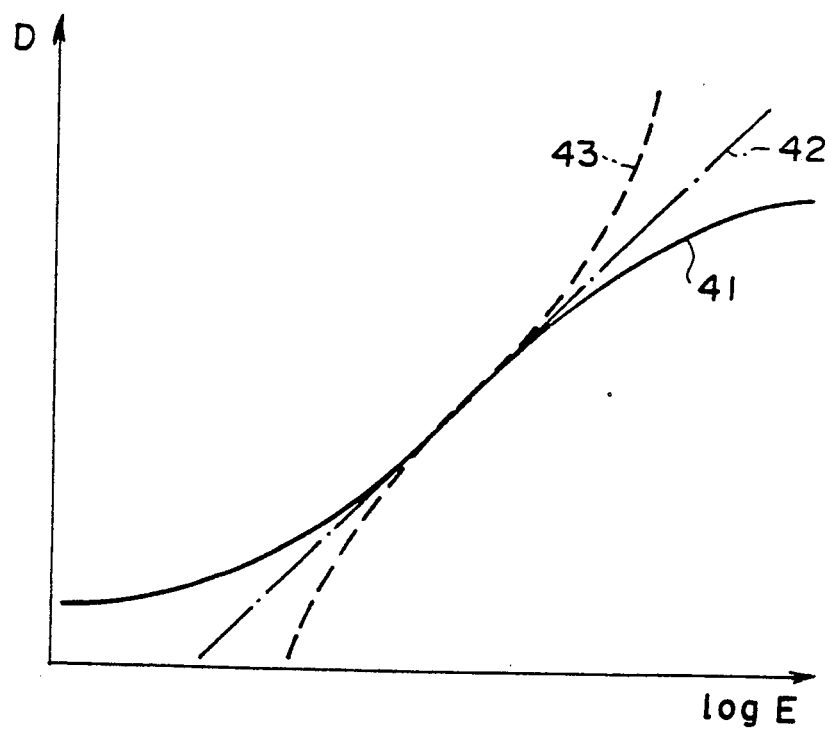
FIG. 2 is a graph showing a characteristic curve of X-ray film, or the like, which graph serves as an aid in explaining how a signal converting process is carried out in a signal conversion means.

FIG. 2 is a graph showing a characteristic curve of X-ray film, or the like, which graph serves as an aid in explaining how a signal converting process is carried out on the first image signal S1 in the signal conversion means 40. In FIG. 2, the amount of energy, E, which has been recorded on the X-ray film 11, is plotted on a logarithmic scale on the horizontal axis (log E), and the image density D of the X-ray image, which has been developed, (i.e. the value of the first image signal S1) with respect to the amount of recorded energy is plotted on the vertical axis.

In FIG. 2, curve 41 indicates the characteristic curve, which is determined by the characteristics of the X-ray film 11. The middle part of curve 41 is approximately straight. At the part of curve 41 from its middle part to the side of the smallest amount of recorded energy (i.e. to the left side of FIG. 2), the change in the image density D with respect to the amount of recorded energy, log E, becomes gradually small. Also, at the part of curve 41 from its middle part to the side of the largest amount of recorded energy (i.e. to the right side of FIG. 2), the change in the image density D with respect to the amount of recorded energy, log E, becomes gradually small. The pattern of curve 41 is determined by the kind of the X-ray film 11.

The signal conversion means 40 stores information about curve 43 as a look-up table. Information about curve 43 is used to convert curve 41 into the characteristic curve (i.e. a straight line 42) of a stimulable phosphor sheet 21, which will be described later. By referring to the look-up table, the signal conversion means 40 converts the image signal components of the first image signal S1, which correspond to picture elements in the X-ray image recorded on the X-ray film 11, into image signal components of a corrected image signal S1' such that the corrected image signal S1' represents the image density following the straight line 42. Thereafter, the corrected image signal S1' is fed into an optical disk storage device (not shown) and stored on an optical disk 50, which has been fitted into the optical disk storage device.

The characteristic curve varies for different kinds of X-ray film. Therefore, a plurality of conversion tables should preferably be prepared in the signal conversion means 40 in accordance with the kinds of X-ray film, and a conversion table appropriate for the X-ray film, from which the X-ray image is read out, should preferably be selected and used in the conversion of the image signal.

Reverting to FIG. 1, in cases where an X-ray image has been stored on a stimulable phosphor sheet 21 in an X-ray image recording apparatus (not shown), the stimulable phosphor sheet 21 is then placed at a predetermined position in a second read-out section 20. The stimulable phosphor sheet 21 is then conveyed in a sub-scanning direction indicated by the arrow Y' by a sheet conveyance means (not shown). A laser beam 24, which serves as stimulating rays, is produced by a laser beam source 23, and is reflected and deflected by a rotating polygon mirror 26 which is quickly rotated by a motor 25 in the direction indicated by the arrow. The laser beam 24 then passes through a converging lens 27 constituted of an $f\theta$ lens or the like. The direction of the optical path of the laser beam 24 is then changed by a mirror 28, and the laser beam 24 impinges upon the stimulable phosphor sheet 21 and scans it in a main scanning direction indicated by the arrow X', which direction is approximately normal to the sub-scanning direction indicated by the arrow Y'. When the stimulable phosphor sheet 21 is exposed to the laser beam 24, the exposed portion of the stimulable phosphor sheet 21 emits light 29 in an amount proportional to the amount of energy stored thereon during its exposure to the X-rays. The emitted light 29 is guided by a light guide member 30 and then photoelectrically detected by a photomultiplier 31. The light guide member 30 is made from a light guiding material such as an acrylic plate and has a linear light input face 30a, positioned so that it extends along the main scanning line on the stimulable phosphor sheet 21, and the ring-shaped light output face 30b, positioned so that it is in close contact with a light receiving face of the photomultiplier 31. The emitted light 29, which has entered the light guide member 30 at its light input face 30a, is guided through repeated total reflection inside of the light guide member 30, emanates from the light output face 30b, and is received by the photomultiplier 31. In this manner, the amount of the emitted light 29, which amount represents the X-ray image, is converted into an electric signal by the photomultiplier 31.

An analog output signal S0 generated by the photomultiplier 31 is logarithmically amplified by a logarithmic amplifier 32, and digitized by an A/D converter 33 into a second digital image signal S2.

The second image signal S2 represents the image density following the straight line 42 shown in FIG. 2. The second image signal S2 is not subjected to signal conversion. The second image signal S2 is directly fed into the optical disk storage device (not shown) and stored on the optical disk 50.

The corrected image signal S1' and the second image signal S2, which have been stored on the optical disk 50, can then be processed in the same manner. When necessary, the corrected image signal S1' or the second image signal S2 is read from the optical disk 50 and subjected to image processing, such as frequency response emphasis processing. A visible image is then reproduced from the image signal, which has been obtained from the image processing, and displayed on a CRT display device, or the like.

What is claimed is:

1. A radiation image read-out apparatus comprising:
    i) a read-out section for photoelectrically reading out a radiation image from silver halide film, on which said radiation image has been recorded, and thereby generating an image signal representing said radiation image, and
    ii) a signal conversion means for converting said image signal such that distortion in said image signal, which distortion is caused to occur by nonlinear characteristics of said silver halide film, is eliminated, and thereby generating a corrected image signal.

2. An apparatus as defined in claim 1, wherein said read-out section is provided with a film digitizer, which is constituted of a light source for linearly irradiating light to said silver halide film having said radiation image recorded and developed thereon, and a line sensor located facing said light source with said silver halide film intervening therebetween, said line sensor detecting the light, which has been produced by said light source and has passed through said silver halide film.

3. An apparatus as defined in claim 1, wherein said silver halide film is x-ray film.

4. An apparatus as claimed in claim 1, wherein the converted image signal is compensated by said signal conversion means to make up for the fact that the amount of energy which has been recorded on said film is not linearly proportional to the image density of said radiation image.

* * * * *